(12) United States Patent
Tsaliovich

(10) Patent No.: US 6,544,259 B1
(45) Date of Patent: Apr. 8, 2003

(54) HAIR REMOVAL METHOD AND DEVICE

(75) Inventor: Anatoly Tsaliovich, East Brunswick, NJ (US)

(73) Assignee: Unite Productions Inc., Watchung, NJ (US)

( * ) Notice: Subject to any disclaimer, the term of this patent is extended or adjusted under 35 U.S.C. 154(b) by 134 days.

(21) Appl. No.: 09/633,416

(22) Filed: Aug. 7, 2000

(51) Int. Cl.⁷ ............................................... A61B 18/18
(52) U.S. Cl. ........................... 606/36; 606/43; 606/133; 606/210
(58) Field of Search ............................. 606/36, 51, 52, 606/43, 44, 9, 133, 210; 601/2

(56) References Cited

U.S. PATENT DOCUMENTS

| | | | | |
|---|---|---|---|---|
| 5,049,148 A | * | 9/1991 | Mehl | 606/43 |
| 5,364,394 A | * | 11/1994 | Mehl | 606/36 |
| 5,425,728 A | * | 6/1995 | Tankovich | 606/131 |
| 5,470,332 A | * | 11/1995 | Mehl et al. | 606/134 |
| 6,200,326 B1 | * | 3/2001 | Narayanan et al. | 606/133 |

* cited by examiner

*Primary Examiner*—Michael Peffley
*Assistant Examiner*—Kenneth Schopfer
(74) *Attorney, Agent, or Firm*—Rader, Fishman & Grauer PLLC

(57) ABSTRACT

Method of removing hair provides for applying radio frequency radiation to a selected skin zone in conjunction with applying ultrasound waves to the skin zone, with pulling the slackened hair out. A combination of a radio frequency generator, and an oscillator that are connected to tweezers constitute a hair removal device implementing the method. A radio frequency power selector enables selecting a suitable mode of operation depending on the texture of skin and its sensitivity.

16 Claims, 6 Drawing Sheets

HAIR REMOVAL METHOD AND DEVICE

BACKGROUND OF THE INVENTION

1. Field of the Invention

The present invention relates to a method of removing hair and hair removal device that make use of a combination of two physical principles by applying radio frequency (RF) field and ultrasound vibrations to hair and their follicles.

2. Description of the Related Art

Recent hair removal or epilator devices currently in use are tweezers type units through which radio frequency (RF) energy is applied to the hair shaft. Typical of such devices and methods for removal of hair are described in U.S. Pat. Nos. 4,174,713; 4,566,454; and 5,049,148; each of which is hereby incorporated by reference as if fully set forth herein. The methods taught in the above-mentioned patents require in many instances thirty seconds treatment of each hair to be removed. Sufficient time was required in order to effectively damage the follicles (root system) of the hair. In such a way, the hair may be removed by a very gentle upward lift rather than by the sharp tug, which would be normally applied for the removal of a single hair by a tweezers without any treatment of the hair. Specifically, U.S. Pat. No. 4,566,454 discloses utilizing the resonant frequency of hair in conjunction with RF.

More recently, an even faster hair removal system, which, by use of RF energy, yielded damage to the root in less than half the time required by earlier methods, is disclosed in U.S. Pat. No. 5,364,394, which is incorporated herein by reference. There are likewise known U.S. Pat. Nos. 5,226,907 and 5,425,728, which disclose using the wave energy of a laser in conjunction with hair removal by the application of a contaminant oil on the skin.

A system for permanent removal of multiple hairs disclosed in the U.S. Pat. No. 5,470,332 includes an adhesive layer, a structural layer disposed adjacent the adhesive layer, and a conductive material. The conductive material functions to provide power from a power source to hairs to be treated that extend up through the adhesive layer and contact the conductive material. A method of removing multiple hairs and inhibiting future hair growth includes the steps of applying a conductive solution to the skin, pressing on an adhesive layer, applying power for a period of time sufficient to destroy the matrix area of the hair, and allowing the treated hair to either be removed immediately or to stay in the skin for a period of time sufficient for the chemical reaction induced at the matrix area to continue long enough to destroy the matrix area and prevent regrowth of the hair. The preferred sources of power include DC power, radio frequency power, galvanic thermolysis, and combinations thereof, such as DC-biased RF or blend.

Method of removing hair from the body and inhibiting future growth disclosed in U.S. Pat. No. 5,846,252 provides for the removal through the use of electromagnetic (e.g., AC, DC, blend, and laser) energy by treatment of the hair prior to the application of such electromagnetic energy to reduce the electromagnetic energy resistance of the hair. Such hair treatment may include applying conductive solutions, pre-treating the hair to yield an alkaline environment (i.e., hair is made more alkaline), and adding graphite, metal, conductive non-metal solids, viscous materials, and liquids.

Also known in the art is a Japanese patent application No. 02-279107 published on Nov. 15, 1990, and describing a method and device for ultrasonic depilation. The device contains an oscillation circuit supplying ultrasonic vibrations to a vibrator that is provided with a pick adapter ending with a pair of pick pieces. When a hair is held by the pick pieces, the ultrasonic vibration is transferred to the hair. In such a way, while allowing the ultrasonic vibration to work on the root of the hair to draw it out, the hair is drawn out gradually by its peak. When tensile force, for instance, of 50 to 100 g per piece is allowed to work, the bonding strength between the root and the skin weakens, "and the depilation can be executed smoothly without allowing a man to feel a pain so much."

WO 93/04636 describes a method based on the observation that by mixing a conductive gel with a treating product, for example a lotion for producing atrophy of the hair roots, it was possible by high-frequency transcutaneous induction to cause the treating product to penetrate into the hair follicles and hence carry out a treatment. The method hence enables a treatment of the skin to be carried out, notably a cosmetic treatment, for example to achieve long lasting depilation. It allows a punctual and effective application down to the follicles without a delicate manual intervention. To carry out the method, WO 93/04636 also describes an apparatus comprising a handleable member, for contacting the skin, having a non-conductive body provided with a contact surface adapted to be applied to the skin. This surface comprises a plurality of discrete conductive electromagnetic emission points, for example formed by exposed parts of turns of a solenoid embedded in the body of the contact member. These points are accessible through openings in this surface and are preferably set back with respect to the latter, so that during use of the apparatus, these points may contact conductive gel applied to the skin. These discrete emission points emit a high-frequency flux of electromagnetic energy, advantageously a pure emissive current, supplied by a high-frequency oscillatory power circuit. The handleable member of the above-described apparatus thus forms a focused probe, whose high-frequency energy produces a point-wise action through the loaded gel. By arranging the discrete emission points in a suitable manner on the contact surface, a simultaneous action is obtained on all of the follicles of an area of the skin. For example, the discrete emission points are aligned in one or several rows along an oblong contact surface, whose dimensions are adapted to the part of the body to be treated. Preferably, several interchangeable rigid contact members are provided having contact surfaces of different shapes and/or of different sizes, and possibly also an interchangeable needle fixture, thus enabling treatments suitable for all types of pilosity. The high-frequency electric generator circuit of the apparatus advantageously comprises a high-frequency oscillatory power circuit comprising a transistor connected as a power oscillator in combination with a pair of square-wound self-inductance coils, and an electrode. Thus, the impedance of a treated person's body may be added to that of the self-inductance coils to increase the frequency of the emissive current during use.

The above-described devices lack efficiency as far as quality of removing hair, painlessness of the depilation, and preventing hair regrowth are concerned.

SUMMARY OF THE INVENTION

It is therefore a principal object of the present invention to provide a method for removing hair that, while preserving main advantages of the methods known in the art, would be free of their drawbacks. Another object of the invention is to provide a hair-removing device that could combine high efficiency in action with painlessness and convenience for a user.

The above objective is met in the invention by virtue of a method that comprises in conjunction the steps of applying radio frequency radiation to a selected skin zone, from which hair is to be removed, whereby hair follicles are destroyed, applying ultrasound waves to the skin zone to shake up the hair with the destroyed follicle and thus slacken the union between the hair and the skin zone and underlying area, and pulling the slackened hair out.

The exposure of hair to ultrasound can be supplemented by the action of sonic waves to further add to the effectiveness of the method.

To enhance effectiveness of the method, frequency of sonic waves applied to the skin can sweep. The coincidence of the frequency of the applied sonic waves with a natural frequency of a hair will cause a resonance that will enhance the slackening effect of the sonic waves.

A device for removing hair from body skin according to the method comprises means for electromagnetically destroying hair follicles at a selected skin zone, means for applying mechanical ultrasound waves to the zone for shaking up the hair with the follicles destroyed by the destroying means, to thereby slacken the union between the hair and the skin zone and underlying area, and means for pulling the slackened hair out.

Preferably, the means for destroying hair follicles includes a radio frequency generator, the means for applying ultrasound waves for shaking up the hair with the follicles includes an oscillator, and the means for pulling the slackened hair out includes tweezers.

The device may further advantageously comprise a radio frequency power selector controlling the radio frequency generator. Thus, the intensity of radio frequency radiation can be varied depending on the texture of hair and sensitivity of the selected skin zone.

The device may also comprise means for creating sonic waves, separate from the oscillator or made integral therewith.

The device further comprises a piezoelement generating the mechanical waves, which is controlled by the oscillator. Upon using ultrasound waves only, the oscillator preferably produces an output signal in the range between about 60 kHz and about 300 kHz, whereas the radio frequency generator operating frequency is preferably 27.125 MHz.

BRIEF DESCRIPTION OF THE DRAWING

These and other objects, features and advantages of the present invention will be more clearly understood from the ensuing description when considered with the reference to accompanying drawings wherein.

DESCRIPTION OF THE PREFERRED EMBODIMENT

Figure 1:
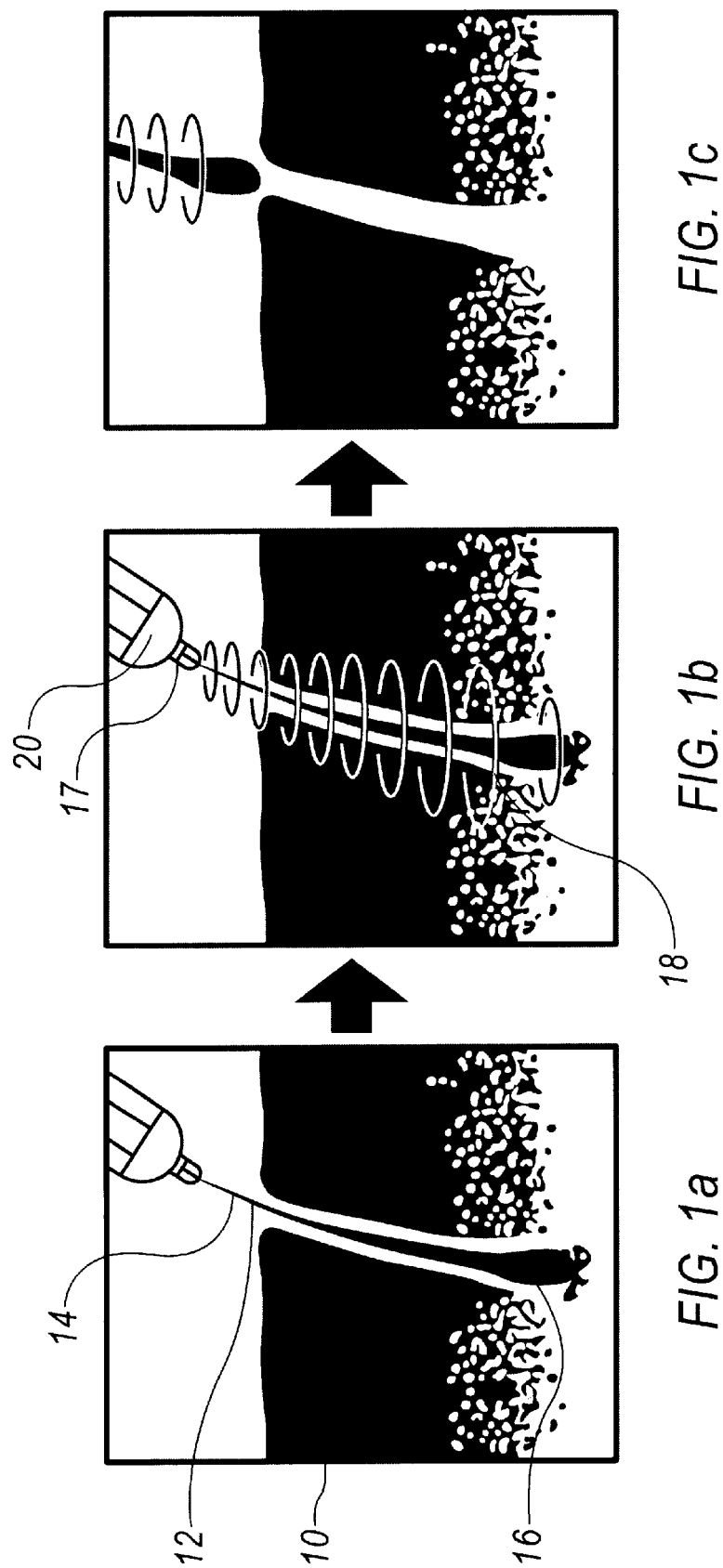
FIGS. 1a–c is an illustration of a general concept of the present invention.

With reference to FIGS. 1a–c, a body skin cover area 10 with a hair 12 having the tip 14 and a follicle 16 is shown, the tip 14 being caught by tweezers tips 17 of a device 20.

According to the method of the present invention, removing the hair 12 first involves applying radio frequency radiation thereto (FIG. 1a). The radiation is destructive for the hair follicle 16 and thus prevents hair from future regrowing. It also makes it easier to subsequently pull out the hair 12 with the follicle 16.

Secondly, ultrasound waves schematically shown in FIG. 1b as a spiral 18 are applied through the tweezers. Ultrasound waves mechanically shake up the follicle 16, already destructed by the radio frequency radiation, as well as the surrounding area. They slacken the union between the hair and the skin zone and underlying area.

To enhance effectiveness of the method, frequency of ultrasound waves applied to the skin can sweep, preferably in the range from about 60 kHz to about 300 kHz.

The exposure of hair to ultrasound can be supplemented by the action of sonic waves to further add to the effectiveness of the method.

After such a hair processing, a step of painless, reliable and convenient depilation itself follows (FIG. 1c). The depilation can be performed through the use of any known technique: it can be performed by tweezers, as well as by applying a patch (that in general is similar, for example, to that disclosed in U.S. Pat. No. 6,039,746 for Patch Electrolysis System And Method For Removing Hair From Skin, which is incorporated herein by reference), with or without the use of a gel, cream, lotion, etc.

Depending on the texture of hair and skin in various body areas and to ensure gentle depilation, a respective power of radio frequency radiation can be selected for, for example, a face mode, arm mode, underarm mode, leg mode, and bikini mode of the method.

Figure 2:
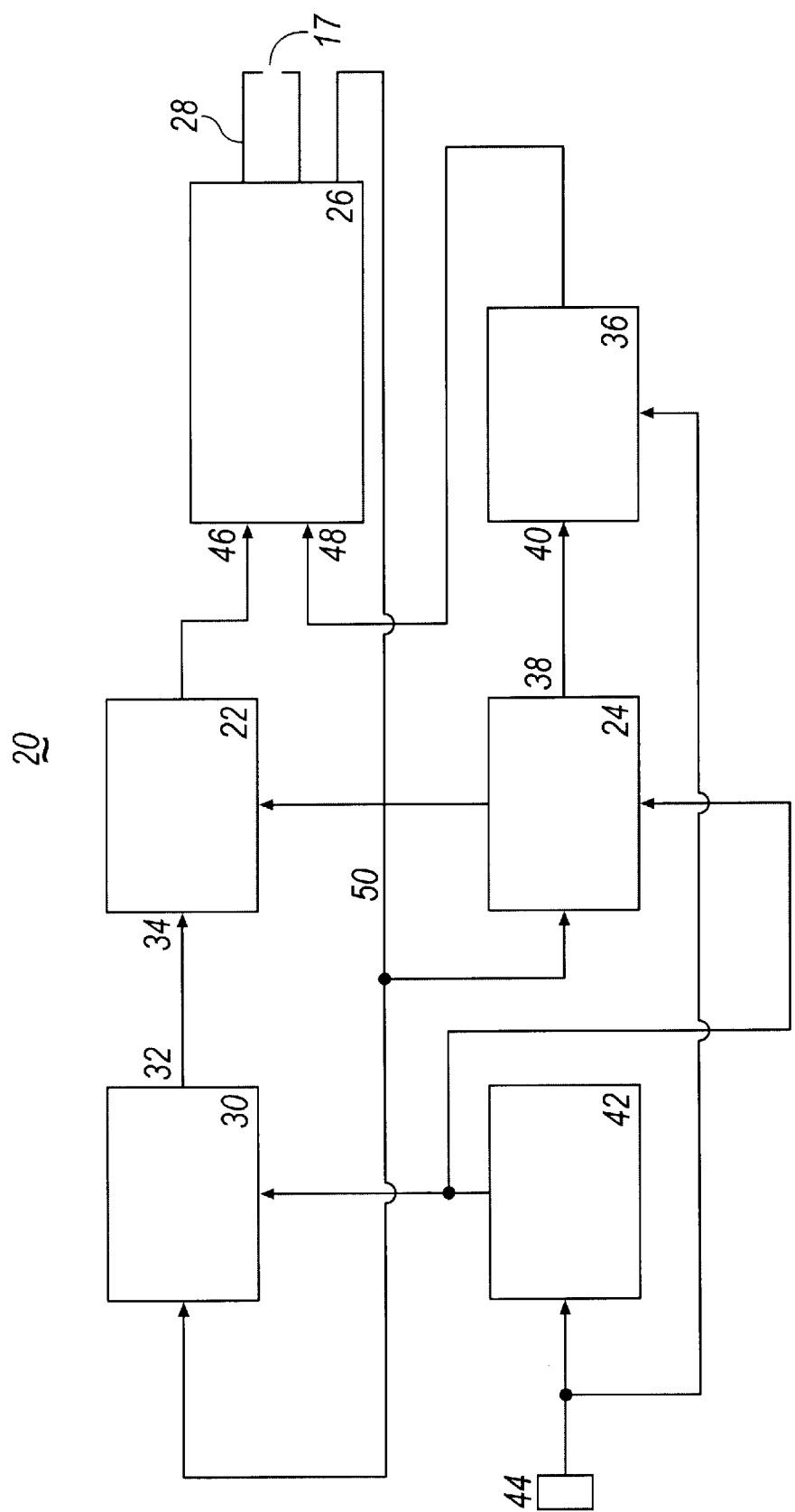
FIG. 2 is a block diagram of a device according to the present invention.

Block diagram of the device 20 implementing the method, as disclosed in the above, is presented in FIG. 2. The device 20 comprises a radio frequency generator 22, an oscillator 24, a wand assembly 26, and tweezers 28. The radio frequency generator 22, preferably operating at 27.125 MHz, can be provided with a power selector 30, whose output 32 is connected to an input 34 of the generator 22. The oscillator 24 preferably operating in the range of about 60–300 kHz is provided with a power amplifier 36, whose purpose is self-explanatory.

A source of sonic waves can be additionally provided to advantageously contribute to the effectiveness of the device. The sonic source can be designed as a separate audio oscillator with a range, for example, from about 5 kHz to about 15 kHz, or combined with the oscillator of ultrasound waves. In the latter case, a traditional waveform generator (square-wave, sawtooth, triangle, etc.) can be conveniently used that is capable of producing a signal, whose harmonics represent sonic and ultrasound waves at preselected frequencies.

An ultrasound signal from an output 38 of the oscillator 24 is fed to an input 40 of the amplifier 36 and to the wand assembly 26 therefrom. A power supply 42 is a source of +12V. In turn, it is fed through a power jack 44 from a source of +31V DC (not shown). It is to be understood that those voltages are given as an example only. Those skilled in the art can power the device in a different way. Specifically, they can easily modify those voltages to fit concrete requirements in various countries, and even make the device battery-fed, without departing from the spirit and scope of the invention as claimed hereinbelow.

The wand assembly 26 serves to accommodate several features of the device 20. It receives output signals from the both generator 22 and oscillator 24 through inputs 46, 48, respectively. The assembly 26 comprises an enable switch (not shown in FIG. 2) that activates an enable line 50 leading to the radio frequency power selector 30 and the oscillator 24. Also, the assembly 26 accommodates a piezoelement (not shown in FIG. 2) that converts power signal into ultrasound waves transmitted to tweezers 28.

Figure 3:
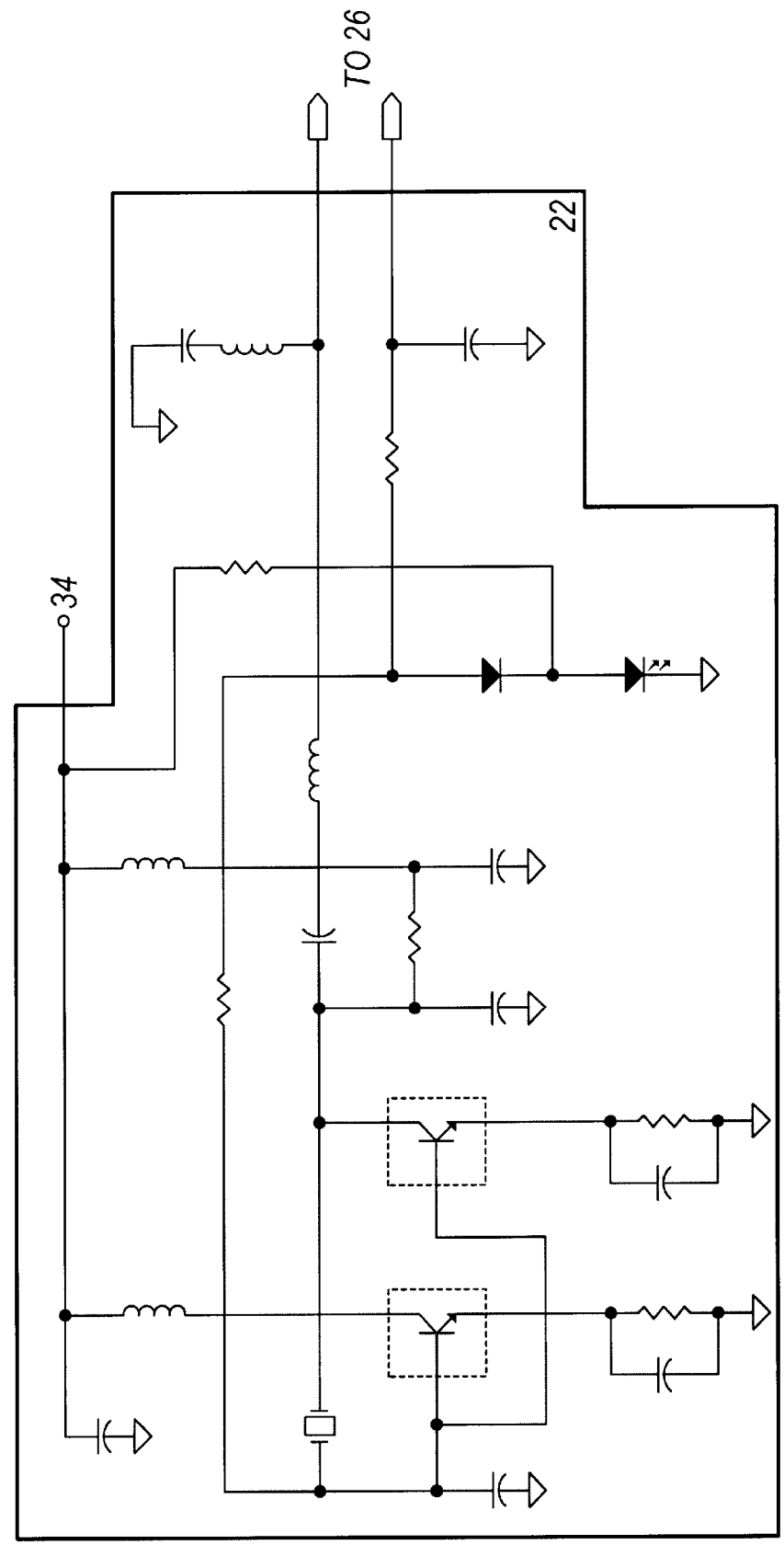
FIG. 3 is a circuit diagram of an exemplary version of a radio frequency generator of the device according to the present invention.
Figure 4:
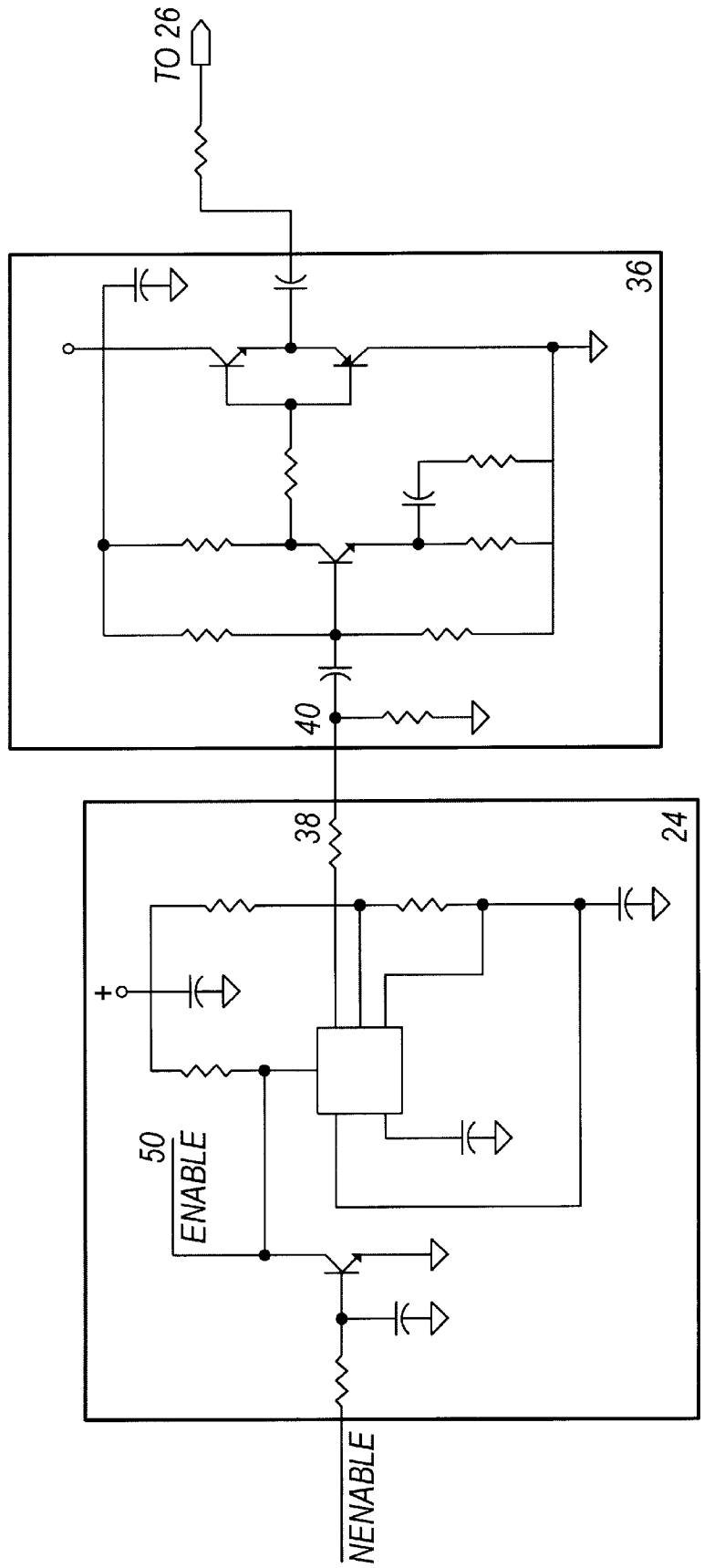
FIG. 4 is a circuit diagram of an exemplary version of an oscillator and power amplifier of the device according to the present invention.
Figure 5:
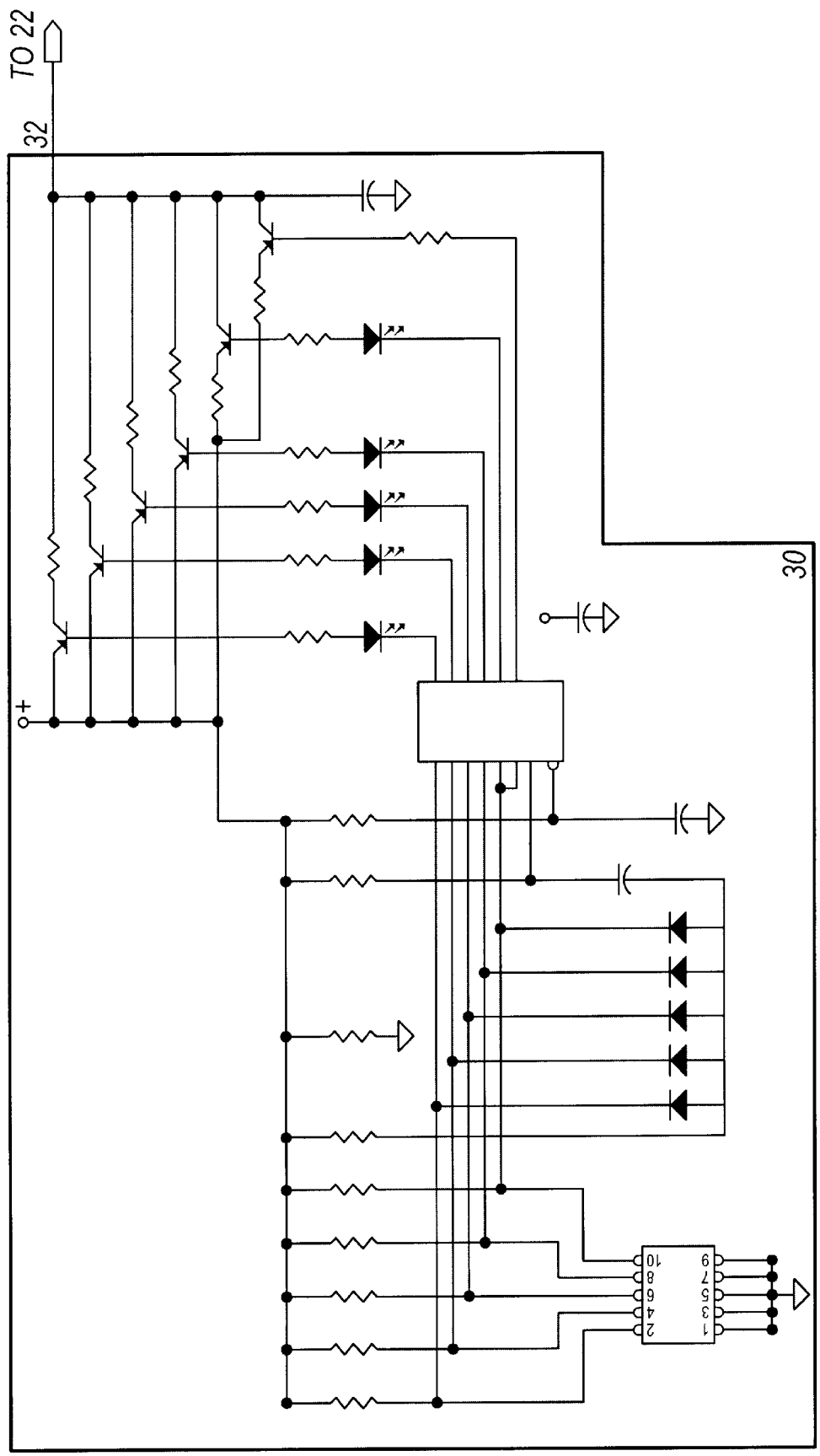
FIG. 5 is a circuit diagram of an exemplary version of a radio frequency power selector of the device according to the present invention.
Figure 6:
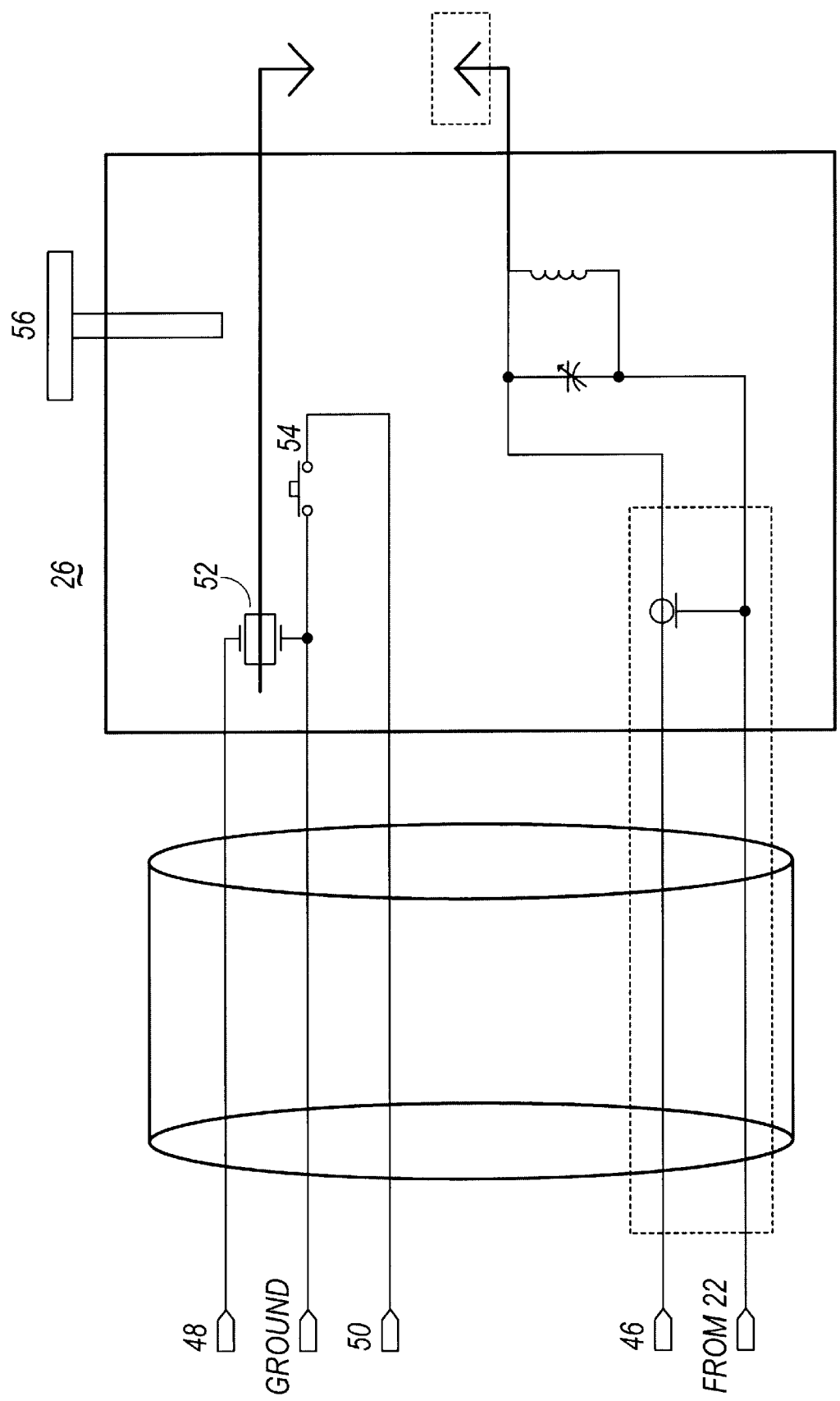
FIG. 6 presents in more detail a wand assembly of the device in accordance with the present invention.

As an example illustrating the implementation of main blocks of the device 20, FIGS. 3–5 show circuit diagrams of the radio frequency generator 22, oscillator 24 with the power amplifier 36, and the radio frequency power selector 30, respectively. FIG. 6 is an illustration in more detail of the wand assembly 26 with the tweezers 28. It is in FIG. 6 that the piezoelement 52, the enable switch 54 and an activation button 56 are presented. ENABLE/NENABLE signals are generated in the assembly 26 serving the purpose of starting the generator 22 and oscillator 24. A coaxial cable is preferably used for wand cable to provide a certain degree of shielding from radiation and independence of cable parameters on the environment. This is important because the capacitance and inductance of the cable determines its resonant properties at 27.125 MHz and thus the voltage at the wand. Otherwise, without such shielding, the cable capacitance will depend on how close to (or far from) other conductors and ground planes the cable is.

In operation of the device 20, it is directed to a selected area, the tweezers 18 engage hair, and the device is turned on as soon as tweezers 28 are compressed. When tips 17 touch each other, it enables both RF and ultrasound portions of the device to turn on. The RF radiation and ultrasound waves are applied to the area, and hair easily and painlessly yield to tweezers 18 pulling them out. The power selector 30 provides a preselected level of radio frequency radiation within a preferable range of 15–90 V peak-to-peak, depending on the texture of hair and skin in various body areas and to ensure gentle depilation. Selected in such a way can be, for example, a face mode, arm mode, underarm mode, leg mode, and bikini mode.

Whereas the use of radio frequency radiation for hair depilation has been known, and whereas it has been known in the art to use ultrasound radiation to remove hair, and whereas there has long been an unsatisfied need for more effective and efficient method and device for hair removal that would be more effective and, at the same time, less troublesome for users, applicant is unaware of any publication where such conjunctive use of radio frequency radiation and ultrasound waves is disclosed, discussed, taught, or suggested.

On this basis, the inventive step of combining two features separately known in the art is believed to be non-obvious.

With regard to the embodiment of the present invention that was disclosed hereinabove, it is to be understood that this embodiment is given by example only and not in a limiting sense. Those skilled in the art may make various modifications and additions to the embodiment chosen to illustrate the invention without departing from the spirit and scope of the present contribution to the art. For example, RF and ultrasound portions may be operated simultaneously or successively. Hair affected by the RF radiation and ultrasound waves can be sucked out, etc. Accordingly, it is to be realized that the patent protection sought and to be afforded hereby shall be deemed to extend to the subject matter claimed and all equivalence thereof fairly within the scope of the invention.

What is claimed is:

1. A method of removing hair from body skin comprising the steps of applying radio frequency radiation to a skin zone, which hair is to be removed from, to thereby destroy hair follicle, in conjunction with applying ultrasound waves to the area to shake up the hair with the destroyed follicle and thus slacken the union between the hair and the skin zone and underlying area, and pulling the slackened hair out.

2. The method according to claim 1, further comprising applying sonic waves to the skin zone.

3. A device for removing hair from body skin comprising means for destroying hair follicles at a selected skin zone, means for applying ultrasound waves for shaking up the hair with the follicles destroyed by said destroying means, to thereby slacken the union between the hair and the skin zone and underlying area, and means for pulling the slackened hair out.

4. The device according to claim 3, wherein said means for destroying hair follicles includes a radio frequency generator.

5. The device according to claim 3, wherein said means for applying ultrasound waves includes an oscillator.

6. The device according to claim 3, wherein said means for pulling the slackened hair out includes tweezers.

7. The device according to claim 3, further comprising means for applying sonic waves for shaking up the hair with the follicles destroyed by said destroying means.

8. The device according to claim 7, wherein said means for applying sonic waves and said means for applying ultrasound waves include a waveform generator to produce a signal, whose harmonics represent sonic and ultrasound waves at preselected frequencies.

9. A device for removing hair from body skin comprising:

a radio frequency generator for destroying hair follicles at a selected skin zone, an oscillator to generate ultrasound waves for shaking up the hair with the follicles destroyed by said radio frequency generator, to thereby slacken the union between the hair and the skin zone and underlying area, and means for pulling the slackened hair out, said radio frequency generator and said oscillator being connected to said means.

10. The device according to claim 9, wherein said means for pulling the slackened hair out includes tweezers.

11. The device according to claim 9, further including a radio frequency power selector controlling said radio frequency generator, to thereby vary the intensity of radio frequency radiation depending on the texture of hair and sensitivity of the selected skin zone.

12. The device according to claim 9, further comprising a piezoelement generating said ultrasound waves, said piezoelement being controlled by said oscillator.

13. The device according to claim 9, wherein said oscillator produces an output signal in the range between about 30 kHz and about 300 kHz.

14. The device according to claim 9, wherein said radio frequency generator produces an output signal at about 27.125 MHz.

15. The device according to claim 9, further comprising an audio oscillator producing an output signal at frequencies ranging from about 5 kHz to about 15 kHz.

16. The device according to claim 15, wherein said oscillator to generate ultrasound waves and said audio oscillator are made as a single waveform generator to produce a signal, whose harmonics represent sonic and ultrasound waves at preselected frequencies.

* * * * *

UNITED STATES PATENT AND TRADEMARK OFFICE
CERTIFICATE OF CORRECTION

PATENT NO.     : 6,544,259 B1
DATED          : April 8, 2003
INVENTOR(S)    : Anatoly Tsaliovich It is certified that error appears in the above-identified patent and that said Letters Patent is hereby corrected as shown below:

<u>Title page,</u>
Item [73], Assignee, the portion of Assignee name reading "Unite" should read
-- United --

Signed and Sealed this

Twenty-ninth Day of July, 2003

JAMES E. ROGAN
*Director of the United States Patent and Trademark Office*